US012806440B2

(12) United States Patent
Yeung et al.

(10) Patent No.: US 12,806,440 B2
(45) Date of Patent: Nov. 24, 2026

(54) GROOMING DEVICE FOR ANIMALS WITH ASYNCHRONOUS INTERMITTENT LIGHT EXPOSURE

(71) Applicant: The Hong Kong University of Science and Technology, Kowloon (CN)

(72) Inventors: King Lun Yeung, Kowloon (CN); Trixie Ruth Nuñez Dy, Kowloon (CN); Leslie Anne Lopez Yasis, Kowloon (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 87 days.

(21) Appl. No.: 19/056,835

(22) Filed: Feb. 19, 2025

(65) Prior Publication Data

US 2025/0262455 A1 Aug. 21, 2025

Related U.S. Application Data

(60) Provisional application No. 63/555,909, filed on Feb. 21, 2024.

(51) Int. Cl.
*A61N 5/06* (2006.01)
*A01K 13/00* (2006.01)

(52) U.S. Cl.
CPC .......... *A61N 5/0624* (2013.01); *A01K 13/002* (2013.01); *A61N 5/0625* (2013.01);
(Continued)

(58) Field of Classification Search
CPC .... A01K 13/00; A01K 13/003; A01K 13/001; A01K 13/002; A61N 5/0617; A61N 2005/0644
See application file for complete search history.

(56) References Cited

U.S. PATENT DOCUMENTS 7,144,247 B2 * 12/2006 Black .................. A61N 5/0603 433/29
2004/0193236 A1 * 9/2004 Altshuler ............ A61B 18/203 607/88

(Continued)

FOREIGN PATENT DOCUMENTS

CA 2884479 A1 * 3/2014 ............ B26B 19/44
CA 2896011 A1 * 6/2014 ............ A61H 7/005

(Continued)

OTHER PUBLICATIONS

"Turn on The Blue"; printed on Nov. 19, 2024 from https://turnontheblue.com/animal-sanitation-with-blue-light-bacteria-killing-light/animal-sanitizing-dog-kennel-disinfection-pet-sanitizer/.

*Primary Examiner* — Monica L Perry
(74) *Attorney, Agent, or Firm* — Nath, Goldberg & Meyer; Jerald L. Meyer; Stanley N. Protigal

(57) ABSTRACT

The grooming device for animals with asynchronous intermittent light exposure combines a grooming tool for an animal with asynchronous intermittent light therapy. The grooming device includes a head portion and a handle portion attached to the head portion. The head portion includes a hollow housing having an upper wall, a lower wall and at least one sidewall. The upper wall has a light exposure aperture formed therethrough. A plurality of light sources are received within the hollow housing. Each of the light sources produces light in a unique wavelength range. The plurality of light sources are positioned within the hollow housing such that the light generated thereby passes through the light exposure aperture. A grooming accessory is releasably attached to the head portion. A controller is configured to actuate selected ones of the plurality of light sources at preselected times with respect to one another and for preselected intervals.

8 Claims, 9 Drawing Sheets

(52) U.S. Cl.
CPC ................. *A61N 2005/0644* (2013.01); *A61N 2005/0659* (2013.01); *A61N 2005/0661* (2013.01); *A61N 2005/0663* (2013.01)

(56) References Cited

U.S. PATENT DOCUMENTS

| | | | | |
|---|---|---|---|---|
| 2005/0166863 | A1* | 8/2005 | Park | A01K 13/00 119/625 |
| 2014/0135798 | A1* | 5/2014 | David | A61B 17/3205 606/131 |
| 2021/0375167 | A1 | 12/2021 | Lin | |
| 2025/0331497 | A1* | 10/2025 | Zhu | A46B 15/0044 |

FOREIGN PATENT DOCUMENTS

| | | | | | |
|---|---|---|---|---|---|
| CN | 110915709 | A | * | 3/2020 | A46B 9/023 |
| KR | 20090120375 | A | * | 11/2009 | A46B 15/0034 |
| KR | 20180060155 | A | | 6/2018 | |
| KR | 20200097985 | A | * | 8/2020 | A01K 13/001 |
| KR | 102184064 | B1 | | 12/2020 | |
| KR | 102307558 | B1 | | 9/2021 | |
| KR | 20240000149 | A | * | 1/2024 | A01K 13/002 |
| KR | 102826297 | B1 | * | 6/2025 | A46B 17/08 |
| KR | 102848211 | B1 | * | 8/2025 | A46B 11/0072 |
| WO | WO-2019072205 | A1 | * | 4/2019 | A61L 2/24 |

* cited by examiner

GROOMING DEVICE FOR ANIMALS WITH ASYNCHRONOUS INTERMITTENT LIGHT EXPOSURE

CROSS-REFERENCE TO RELATED APPLICATIONS

This application claims the benefit of U.S. Provisional Patent Application No. 63/555,909, filed on Feb. 21, 2024.

BACKGROUND

Field

The disclosure of the present patent application relates to animal grooming and care, and particularly to a grooming device for animals which also treats microbial infection and pest infestation using asynchronous light exposure.

Description of Related Art

Caring for an animal's coat and skin is of critical importance for the overall health and well-being of the animal. Various harmful microbes, including bacteria, fungi, mold and viruses, can infect an animal's skin, leading to infection and disease. Animals also experience irritation and potential health risks due to infestation by various types of pests, such as fleas, ticks and lice. The bites of such pests can potentially lead to anemia, the transmission of parasites (e.g., tapeworms), and the transmission of diseases, such as Bartonellosis.

Caring for an animal's coat of fur is also important for the animal's overall health, since infestations of the coat can not only cause the coat to become dull, matted and unmanageable, but can also lead to physical discomfort for the animal. Additionally, mange, for example, which is caused by mite infestation, results in scratching and biting, potentially leading to open sores and infections. In addition to the health of the animal, the presence of microbial life and pests in an animal's coat and on its skin can pose a risk to human health. Fleas and ticks, for example, can be transferred from animals to humans.

Although treatment of various skin conditions of animals is common, as is general grooming and cleaning of animals, the two are typically considered separate care-related activities, not only performed at different times but by different professionals. If the two could be easily combined, it would save time, money and potentially provide the animal with quicker relief. Additionally, treatment of microbial infections and pests is typically performed using chemicals and/or pharmaceuticals. Both types of treatments are not only costly but can be potentially harmful to the animal due to misapplication, allergic reactions, and side-effects. Thus, a grooming device for animals with asynchronous intermittent light exposure solving the aforementioned problems is desired.

SUMMARY

The grooming device for animals with asynchronous intermittent light exposure combines a grooming tool for an animal, such as a brush for a dog or cat's fur, as a non-limiting example, with asynchronous intermittent light therapy for treating microbial growth, repelling pests, such as ticks and fleas, and promoting healthy skin and fur. The grooming device includes a head portion and a handle portion which is attached to the head portion. The head portion includes a hollow housing having an upper wall, a lower wall and at least one sidewall. The upper wall has a light exposure aperture formed therethrough. A plurality of light sources are received within the hollow housing. Each of the light sources produces light in a unique wavelength range. The plurality of light sources are positioned within the hollow housing such that the light generated thereby passes through the light exposure aperture. A grooming accessory is releasably attached to the head portion. The grooming device further includes a controller configured to actuate selected ones of the plurality of light sources at preselected times with respect to one another and for preselected intervals.

As a non-limiting example, the light sources may be configured to generate light in any of the following wavelength ranges, although each light source generates light in a wavelength range unique from the others: ultraviolet (200±20 nm, 225±20 nm, 250±20 nm, 285±20 nm, 365±20 nm, 385±20 nm, 395±20 nm, 405±20 nm), blue (450±20 nm, 495±20 nm), green (525±20 nm, 570±20 nm), red and near infrared (630±20 nm, 650±20 nm, 700±20 nm, 800±20 nm, 850±20 nm). The light sources may be any suitable type of light sources that can supply high intensity light within narrow wavelength ranges, including, as non-limiting examples, light emitting diodes (LEDs), lasers and laser diodes. The short wavelength ranges, including ultraviolet and blue light, are effective in disinfecting microbes and repelling pests, such as fleas, ticks, mites and lice. Green light is known to treat dilated capillaries and promote skin healing. Red light and near infrared light warm the skin and promote blood circulation. By utilizing the high intensity narrow wavelength lights, the grooming device can effectively target and rapidly eliminate harmful microbes, including viruses, bacteria, fungi and mold, from the animal's skin and coat. This treatment provides a safer alternative to traditional chemical-based treatments that may have harmful side effects on pets.

Non-limiting examples of grooming accessories which may be used with the plurality of light sources include combs, brushes, rakes, slickers, dryers, vacuums, massagers, liquid sprayers and combinations thereof. In use, the grooming device may be used to, as a non-limiting example, clean, comb and massage the coat and skin. The programmable light sources are synchronized with the grooming process to provide a combination of light wavelengths for each stage of grooming. This ensures that the pet's coat and skin are thoroughly cleaned, disinfected and rid of pests.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

Figure 1:
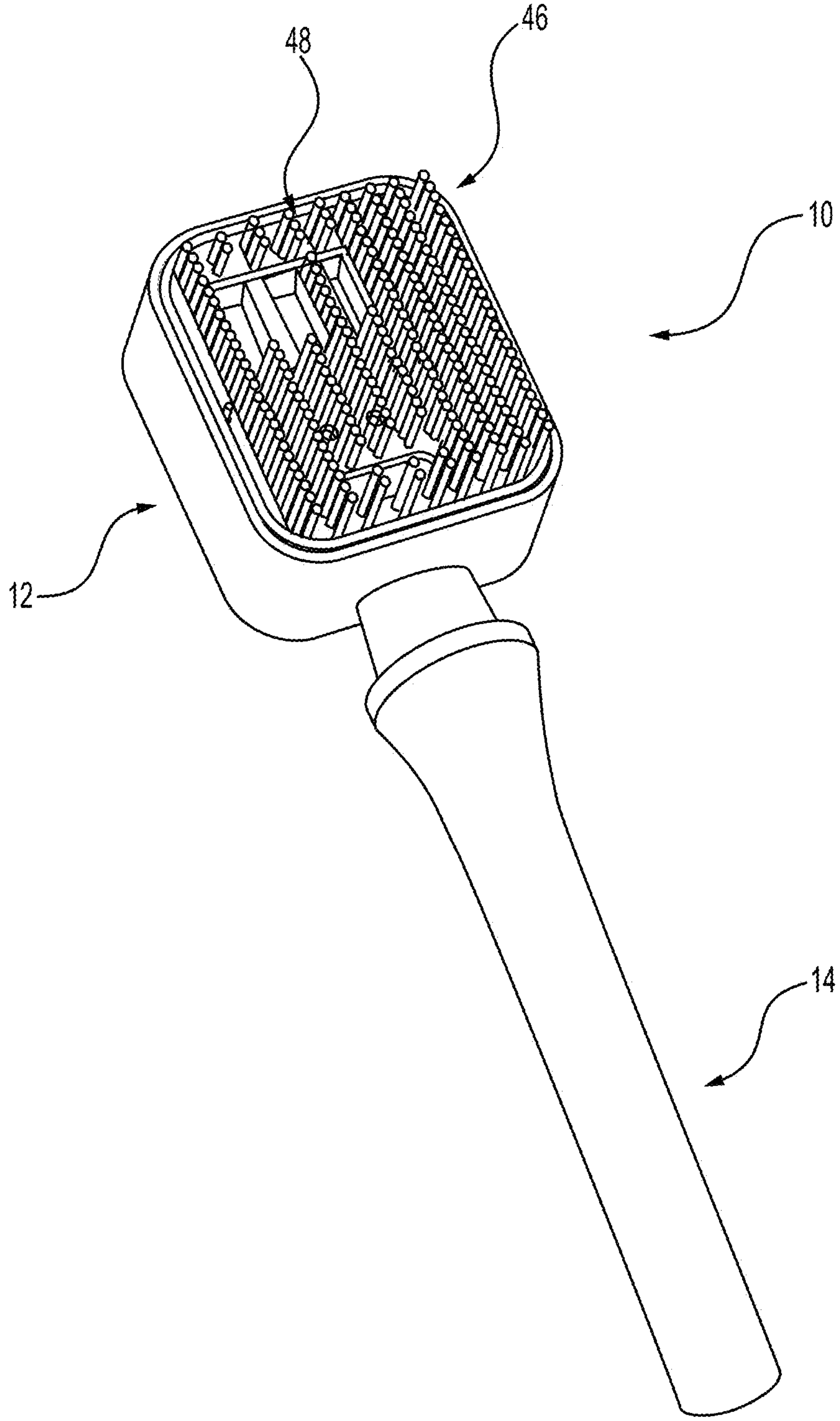
FIG. 1 is a perspective view of a grooming device for animals with asynchronous intermittent light exposure.
Figure 2A:
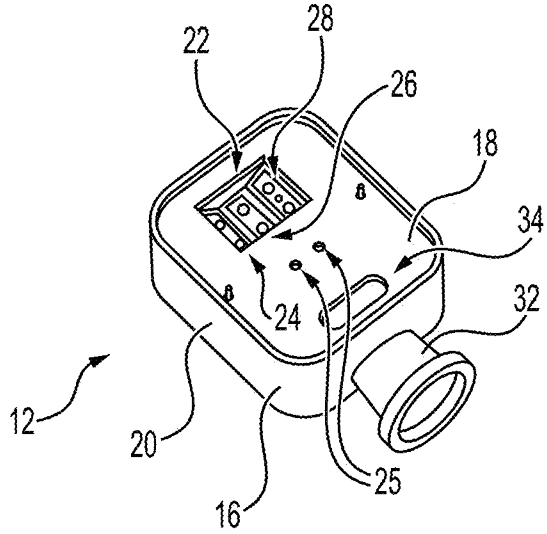
FIG. 2A is a perspective view of a head portion of the grooming device for animals with asynchronous intermittent light exposure.
Figure 2B:
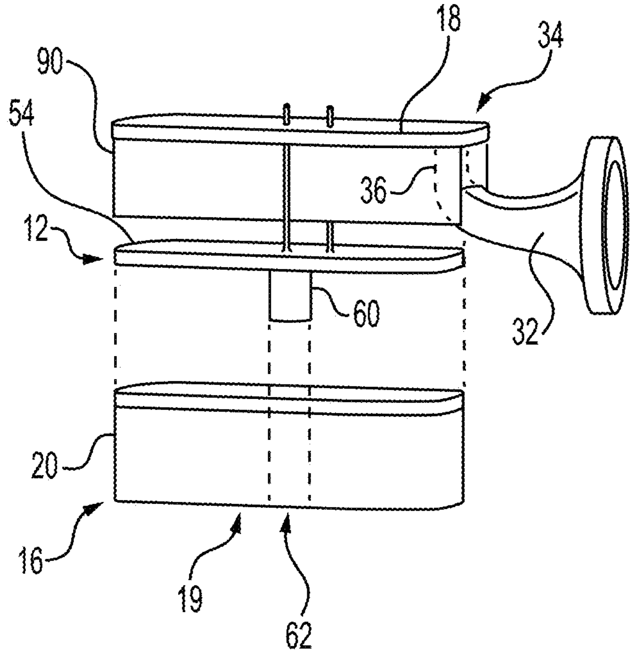
FIG. 2B is a partially-exploded perspective view of the head portion of the grooming device for animals with asynchronous intermittent light exposure.

The grooming device for animals with asynchronous intermittent light exposure 10 combines a grooming tool for an animal, such as a brush for a dog or cat's fur, as a non-limiting example, with asynchronous intermittent light therapy for treating microbial growth, repelling pests, such as ticks and fleas, and promoting healthy skin and fur. As shown in FIG. 1, the grooming device 10 includes a head portion 12 and a handle portion 14 which is attached to the head portion 12. As shown in FIGS. 2A and 2B, the head portion 12 includes a hollow housing 16 having an upper wall 18, a lower wall 19 and at least one sidewall 20. Although the hollow housing 16 is shown as having a substantially rectangular shape in the non-limiting example of FIGS. 1, 2A and 2B, it should be understood that hollow housing 16 and head portion 12 may have any suitable shape and relative dimensions.

As shown in FIG. 2A, the upper wall 18 has a light exposure aperture 22 formed therethrough. A plurality of light sources 24, 26, 28 are received within the hollow housing 16. Although the non-limiting example of FIG. 2A shows three such light sources 24, 26, 28, it should be understood that any suitable number of light sources may be provided. As shown in FIG. 2A, one or more additional light sources 25 may also be added, as desired. Each of the light sources 24, 26, 28 produces light in a unique wavelength range. As a non-limiting example, light sources 24, 26, 28 may be configured to generate light in any of the following wavelength ranges, although each light source should generate light in a wavelength range unique from the others: ultraviolet (200±20 nm, 225±20 nm, 250±20 nm, 285±20 nm, 365±20 nm, 385±20 nm, 395±20 nm, 405±20 nm), blue (450±20 nm, 495±20 nm), green (525±20 nm, 570±20 nm), red and near infrared (630±20 nm, 650±20 nm, 700±20 nm, 800±20 nm, 850±20 nm). It should be understood that light sources 24, 26, 28 may be any suitable type of light sources that can supply high intensity light within narrow wavelength ranges, including, as non-limiting examples, light emitting diodes (LEDs), lasers, and laser diodes.

The short wavelength ranges, including ultraviolet and blue light, are effective in disinfecting microbes and repelling pests, such as fleas, ticks, mites and lice. Green light is known to treat dilated capillaries and promote skin healing. Red light and near infrared light warm the skin and promote blood circulation. By utilizing the high intensity narrow wavelength lights, grooming device 10 can effectively target and rapidly eliminate harmful microbes, including viruses, bacteria, fungi and mold, from the animal's skin and coat. This treatment provides a safer alternative to traditional chemical-based treatments that may have harmful side effects on pets.

The plurality of light sources 24, 26, 28 are positioned within the hollow housing 16 such that the light generated thereby passes through the light exposure aperture 22. As will be discussed in greater detail below, a grooming accessory is releasably attached to the head portion 12. Non-limiting examples of grooming accessories which may be used with the plurality of light sources 24, 26, 28 include combs, brushes, rakes, slickers, dryers, vacuums, massagers, liquid sprayers and combinations thereof. In use, the grooming device 10 may be used to, as a non-limiting example, clean, comb and massage the coat and skin. The programmable light sources 24, 26, 28 are synchronized with the grooming process to provide a combination of light wavelengths for each stage of grooming. This ensures that the pet's coat and skin are thoroughly cleaned, disinfected and rid of pests.

The grooming device 10 further includes a controller 30 configured to actuate selected ones of the plurality of light sources 24, 26, 28 at preselected times with respect to one another and for preselected intervals. The controller 30 may be pre-programmed, with instructions stored in non-transitory computer readable memory 100, to control and adjust the light intensity, pulse the light, and provide asynchronous intermittent lighting. It should be understood that controller 30 may be any suitable type of controller, such as a microprocessor, a programmable logic controller, control circuitry or the like.

Figure 2C:
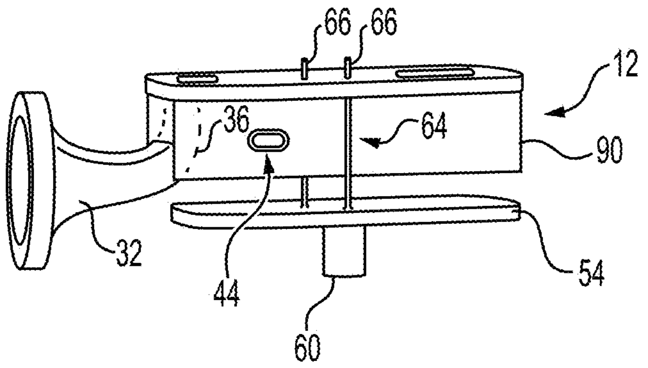
FIG. 2C is a perspective view of the head portion of FIGS. 2A and 2B, shown without a hollow housing thereof.

The handle portion 14 may be releasably attached to the head portion 12 using any suitable type of releasable attachment, such as, but not limited to, magnetic attachments, clamps, clips, snap fasteners or the like. As shown in FIGS. 2A, 2B and 2C, the head portion 12 includes a hollow connection portion 32 for releasable attachment to the handle portion 14. It should be understood that the shape and relative dimensions of the hollow connection portion 32 are shown for exemplary purposes only and may be varied dependent upon the particular size, shape and style of handle portion 14. As shown in FIGS. 2A and 2B, the upper wall 18 of the hollow housing 16 has a fluid port 34 formed therein, and the fluid port 34 is in fluid communication with the hollow connection portion 32. As a non-limiting example, handle portion 14 may be equipped with a reservoir containing water, essential oils, or any other desired fluid. Handle portion 14 may also include a pump 38 which, under control of controller 30, is adapted for selectively pumping the fluid from the reservoir, through the hollow connection portion 32 and through the fluid port 34 (via a connecting conduit 36). Thus, the fluid may be applied to the pet during grooming for, as a non-limiting example, washing the animal's fur or rinsing a cleaning agent from the animal's fur.

Figure 7A:
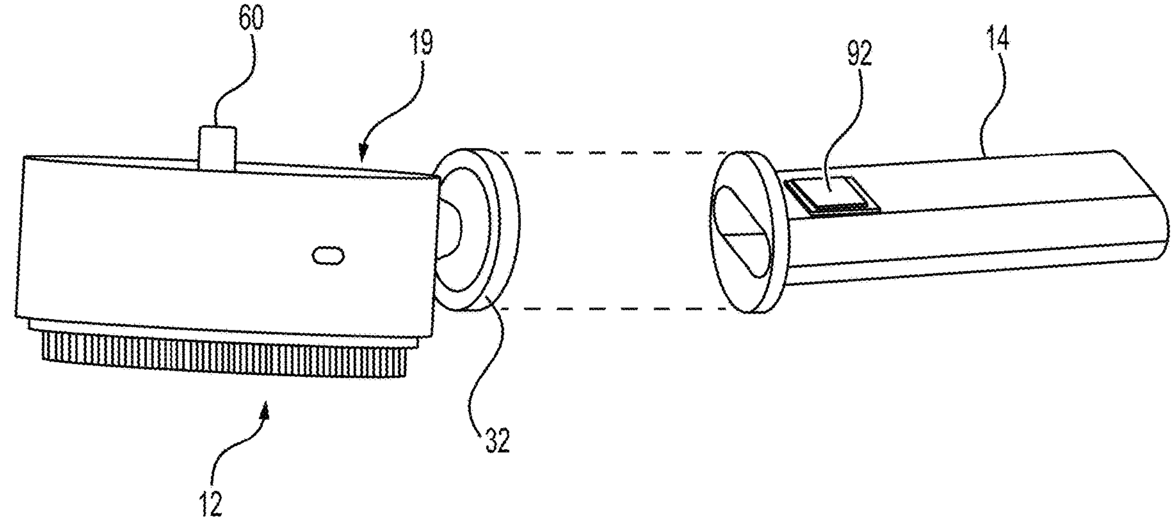
FIG. 7A is a partially exploded view of the grooming device for animals with asynchronous intermittent light exposure.

As another non-limiting example, the handle portion 14 may be equipped with a blower 40 in communication with the controller 30. The blower 40 is adapted for selectively and controllably blowing air through the hollow connection portion 32 and the fluid port 34 (via the connecting conduit 36). As shown in FIGS. 7A, the head portion 12 may be connected to a different handle portion dependent upon the desired need. In the non-limiting example of FIG. 7A, handle portion 14 contains the fluid reservoir and pump 38 for supplying a fluid, with actuation and/or programming being implemented via a user interface 92 (shown in the non-limiting example of FIG. 7A as a simple button). The handle portion 14 may be removed and replaced with the handle portion 94 of FIG. 7B which, as a non-limiting example, may be configured similar to a conventional hair dryer, also programmed and/or actuated by user interface 96 in communication with controller 30. The hair dryer type handle portion 94 includes a blower for delivering heated or cooled air. Handle portion 94 may be used to, as a non-limiting example, dry the animal's fur. As a further non-limiting example, the handle portion may be equipped with a suction fan 42 for vacuuming shed fur and the like. It should be understood that user interfaces 92, 96 may be any suitable type of user interface, including, but not limited to, buttons, keys, switches, wireless interfaces and/or wireless devices, or the like.

Figure 3A:
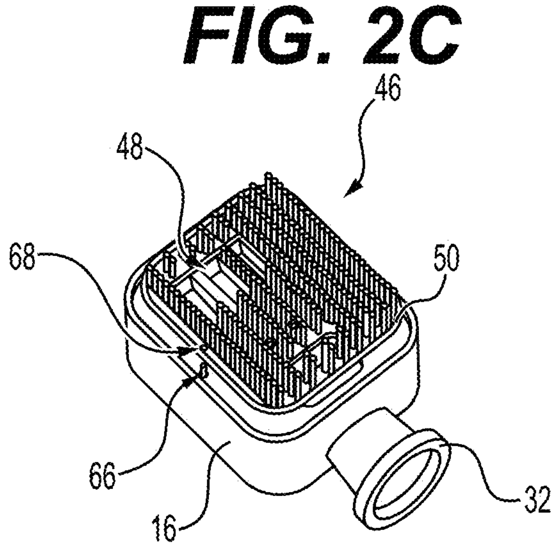
FIG. 3A is a perspective view of the head portion of FIGS. 2A and 2B shown with a brush being attached thereto.
Figure 3B:
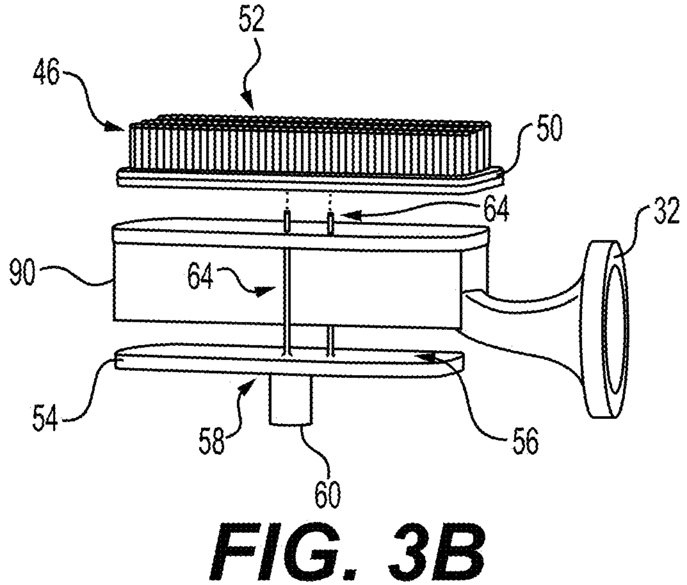
FIG. 3B is a perspective view of the partial head portion of FIG. 2C shown with the brush being attached thereto.

FIGS. 2B-4C illustrate a non-limiting example in which the grooming accessory is a brush 46 which, as shown in FIGS. 3A and 3B, includes a bristle plate 50 releasably attached to the hollow housing 16 and a plurality of bristles 52 fixed to, and projecting from, the bristle plate 50. The bristle plate 50 has a light exposure opening 48 formed therethrough which is aligned with the light exposure aperture 22 formed through upper wall 18 when the bristle plate 50 is releasably attached to the hollow housing 16. This allows the light sources 24, 26, 28 to operate and project light when the brush 46 is attached to the head portion 12. The bristle plate 50, and any other grooming accessories, may be releasably attached to head portion 12 using any suitable type of releasable attachment, such as magnetic attachment, clips, clasps or the like. It should be understood that the size, relative dimensions and overall style of brush 46 are shown for exemplary purposes only.

Figure 7B:
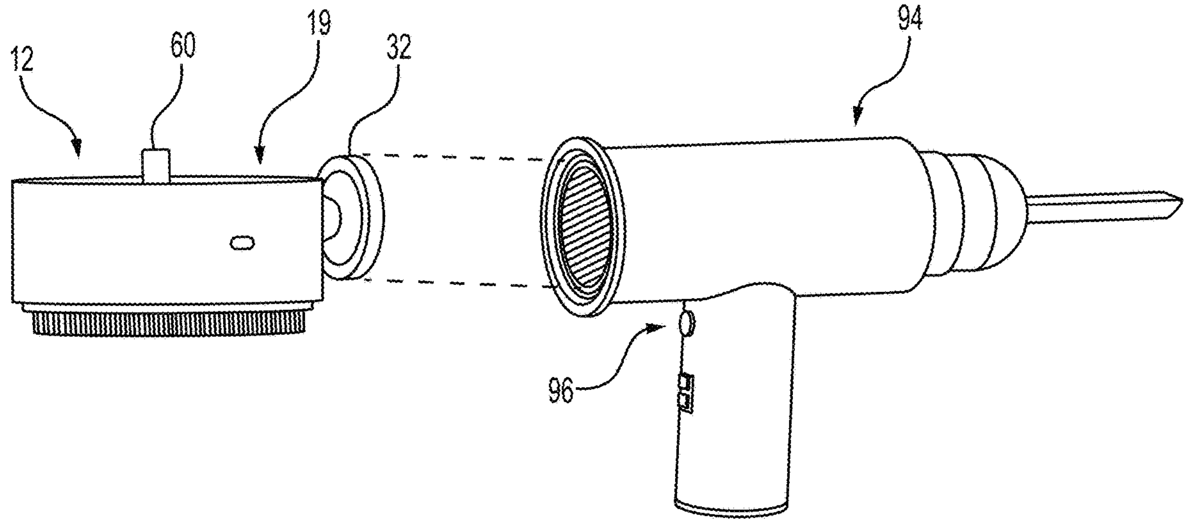
FIG. 7B is a partially exploded view of an alternative configuration of the grooming device for animals with asynchronous intermittent light exposure.

As shown in FIGS. 2B, 2C and 3B, a pusher plate 54 may be received within the hollow housing 16. The pusher plate 54 has opposed upper and lower surfaces 56, 58, respectively. A push button 60 is secured to the lower surface 58 of the pusher plate 54, and the lower wall 19 of the hollow housing 16 has a button opening 62 formed therethrough such that the push button 60 projects outwardly through the button opening 62, as shown in FIGS. 7A and 7B. It should be understood that the shape and relative dimensions of push button 60 are shown for exemplary purposes only. A pair of rods 64 is provided, with each rod 64 having opposed upper and lower ends. The lower ends thereof are secured to the upper surface 56 of the pusher plate 54, and the upper ends 66 are respectively slidably received through a pair of passages 68 formed through the bristle plate 50 (see FIG. 3A). In FIGS. 2B, 2C and 3B, the electronics, including light sources 24, 26, 28, are contained within an enclosure 90 to provide protection for the electronics. The light sources 24, 26, 28 and other electronic components may be powered by, for example, a rechargeable battery, also received within enclosure 90, and which may be recharged via a charging port 44.

Figure 4A:
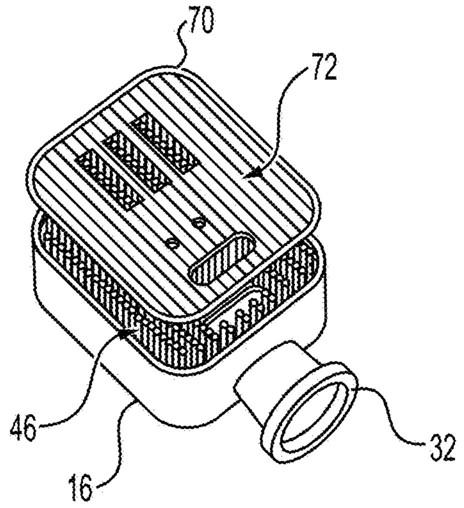
FIG. 4A is a perspective view of the head portion and the brush with a fur removal plate being attached thereto.
Figure 4B:
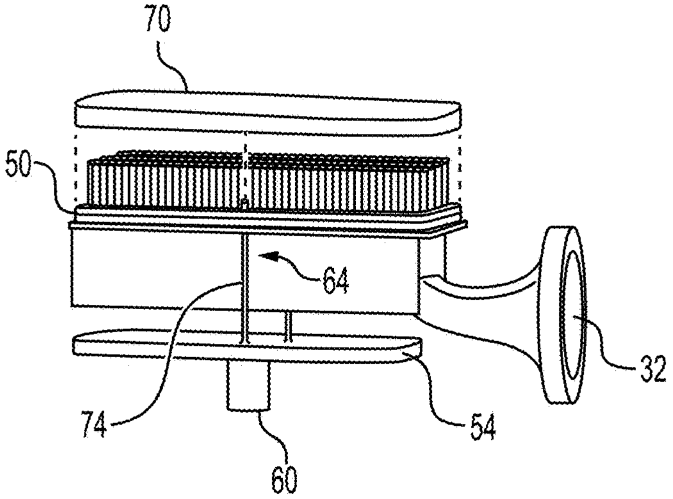
FIG. 4B is a perspective view of the partial head portion of FIG. 2C with the brush, shown with the fur removal plate being attached thereto.
Figure 4C:
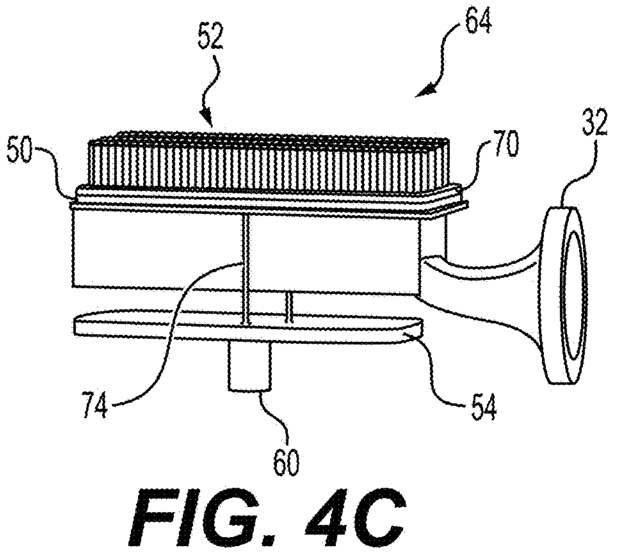
FIG. 4C is a perspective view of the partial head portion of FIG. 2C with the brush and fur removal plate attached thereto.

As shown in FIGS. 4A, 4B and 4C, a fur removal plate 70 may be provided. The fur removal plate 70 has a plurality of slots 72 formed therethrough. The plurality of bristles 52 are slidably received through the slots 72 and the fur removal plate 70 is releasably attached to the upper ends 66 of the pair of rods 64 using a magnetic attachment or the like. FIG. 4C shows the fur removal plate 70 when it is not in use. In this configuration, the fur removal plate 70 is seated on the bristle plate 50, with the bristles 52 fully extending through slots 72. When the user wishes to remove fur from bristles 52, the user pushes the pusher plate 54 upward via the push button 60. This causes the rods 64 to rise with respect to hollow housing 16 which, in turn, pushes the fur removal plate 70 with respect to the bristle plate 50. The bristles 50 slide through the slots 72 as the fur removal plate 70 rises, thus pushing trapped fur upward, along the length of the bristles. As shown in FIGS. 4B and 4C, the rods 64 may be spring biased by a pair of springs 74 respectively wrapped around the pair of rods 64 between the pusher plate 54 and the upper wall 18 of the hollow housing 16.

Figure 5A:
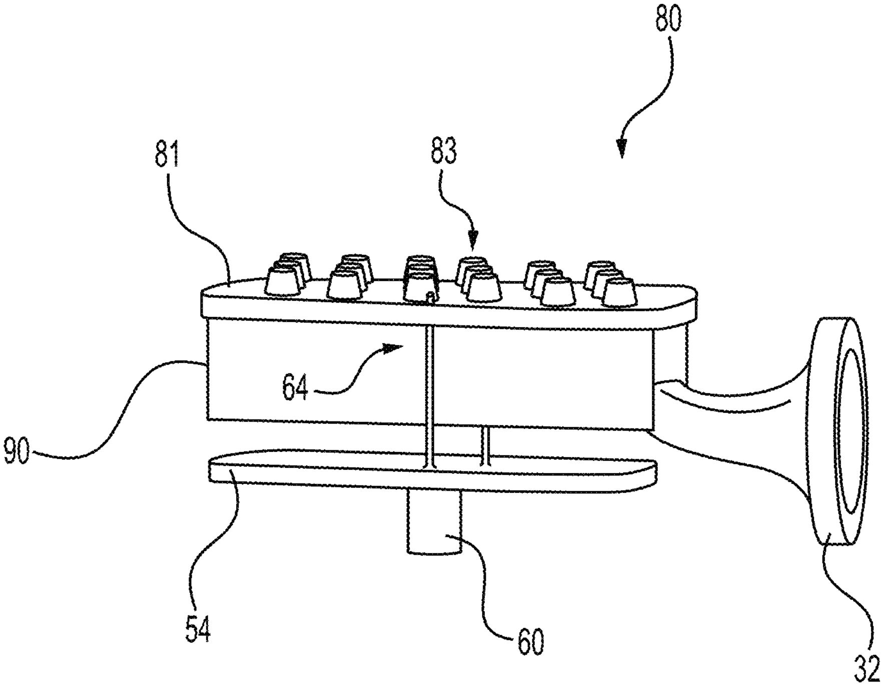
FIG. 5A is a perspective view of the partial head portion of FIG. 2C shown with a massager attached thereto.
Figure 5B:
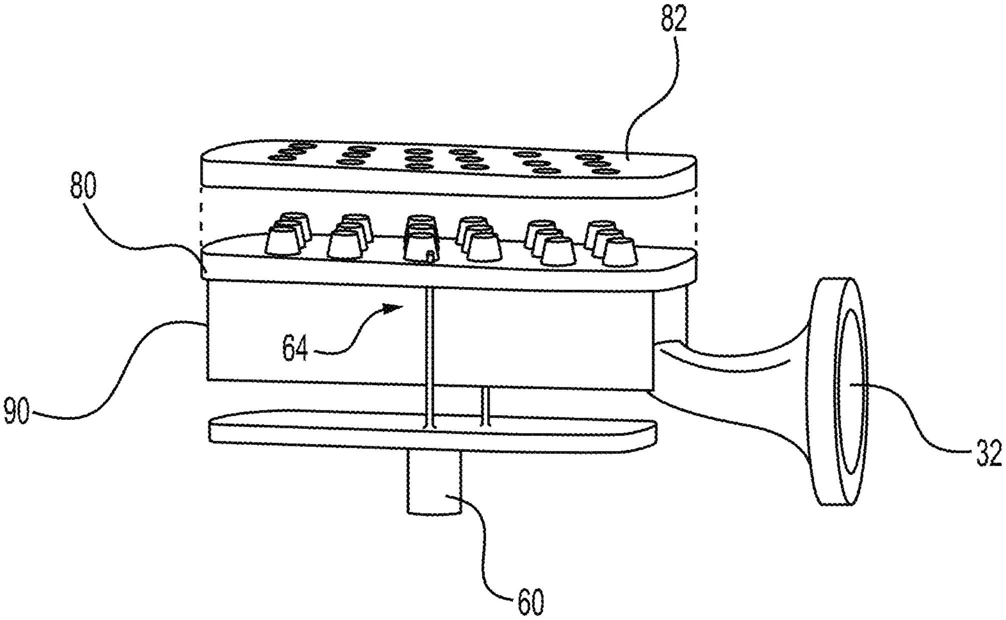
FIG. 5B is a perspective view of the partial head portion and the massager of FIG. 5A, shown with a stabilizing plate being attached thereto.

FIGS. 5A and 5B illustrate another non-limiting example of a removable grooming accessory. In this non-limiting example, the grooming accessory is a massager 80, including a plate 81 with a plurality of projecting massage elements 83. The plate 81 may be releasably attached to head portion 12 using any suitable type of releasable attachment, such as a magnetic attachment, clips, clasps or the like. As shown in FIG. 5B, an additional stabilizing plate 82, which includes a plurality of openings for receiving the massage elements 83, may be attached to plate 81 for holding plate 81 in place and providing stability therefor. As shown, the upper ends of rods 64 may project through plate 81 for attachment to stabilizing plate 82 by magnetic attachment or the like. In use, the stabilizing plate 82 replaces fur removal plate 70 of FIG. 4B and, in addition to providing stabilization, can further be used for the same fur removal function. As shown, the pusher plate 54, push button 60 and rods 64 remain and may be used in a manner similar to their use with the fur removal plate 70.

Figure 6A:
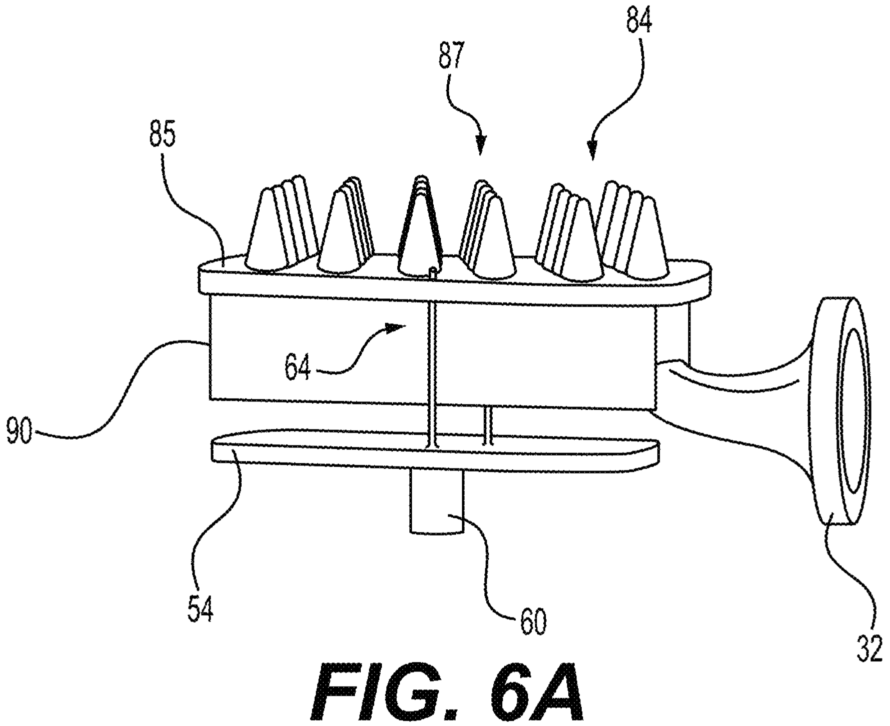
FIG. 6A is a perspective view of the partial head portion of FIG. 2C shown with an alternative massager attached thereto.
Figure 6B:
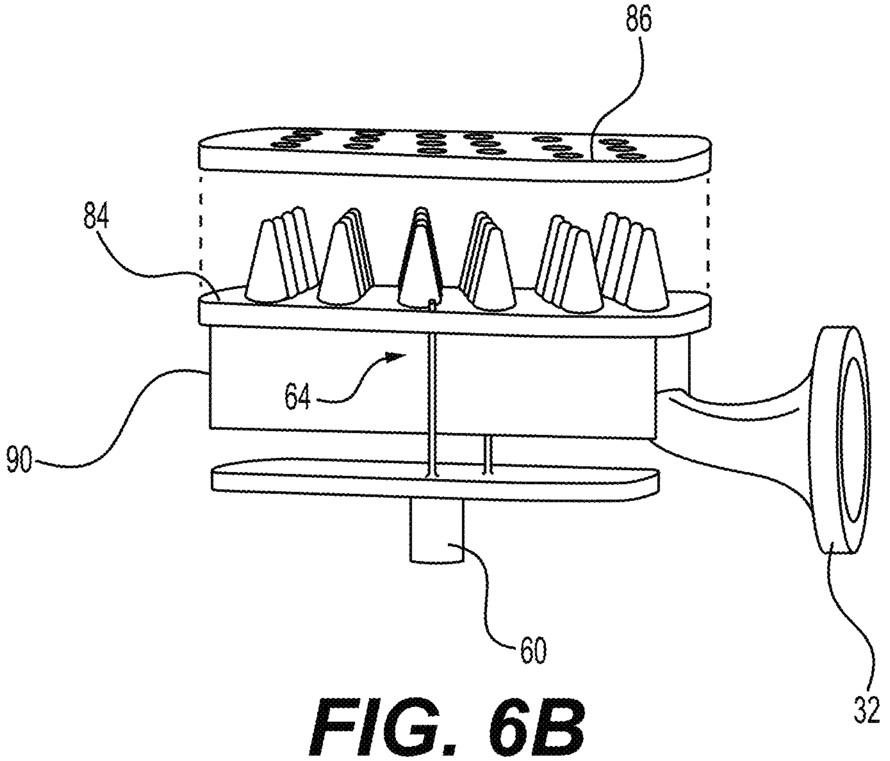
FIG. 6B is a perspective view of the partial head portion and the alternative massager of FIG. 6A, shown with a stabilizing plate being attached thereto.

FIGS. 6A and 6B illustrate another non-limiting example of a massager 84, which is substantially similar to massager 80, including a plate 85, massage elements 87 and a stabilizing plate 86. As shown, massage elements 87 have a different shape and relative dimensions compared with massage elements 83. It should be understood that the massage elements 83, 87 may have any suitable shape and relative dimensions, and may be provided in any suitable number and arrangement. Similar to stabilizing plate 82, the stabilizing plate 86 may also be used in conjunction with the pusher plate 54, push button 60 and rods 64 for fur removal.

Figure 8:
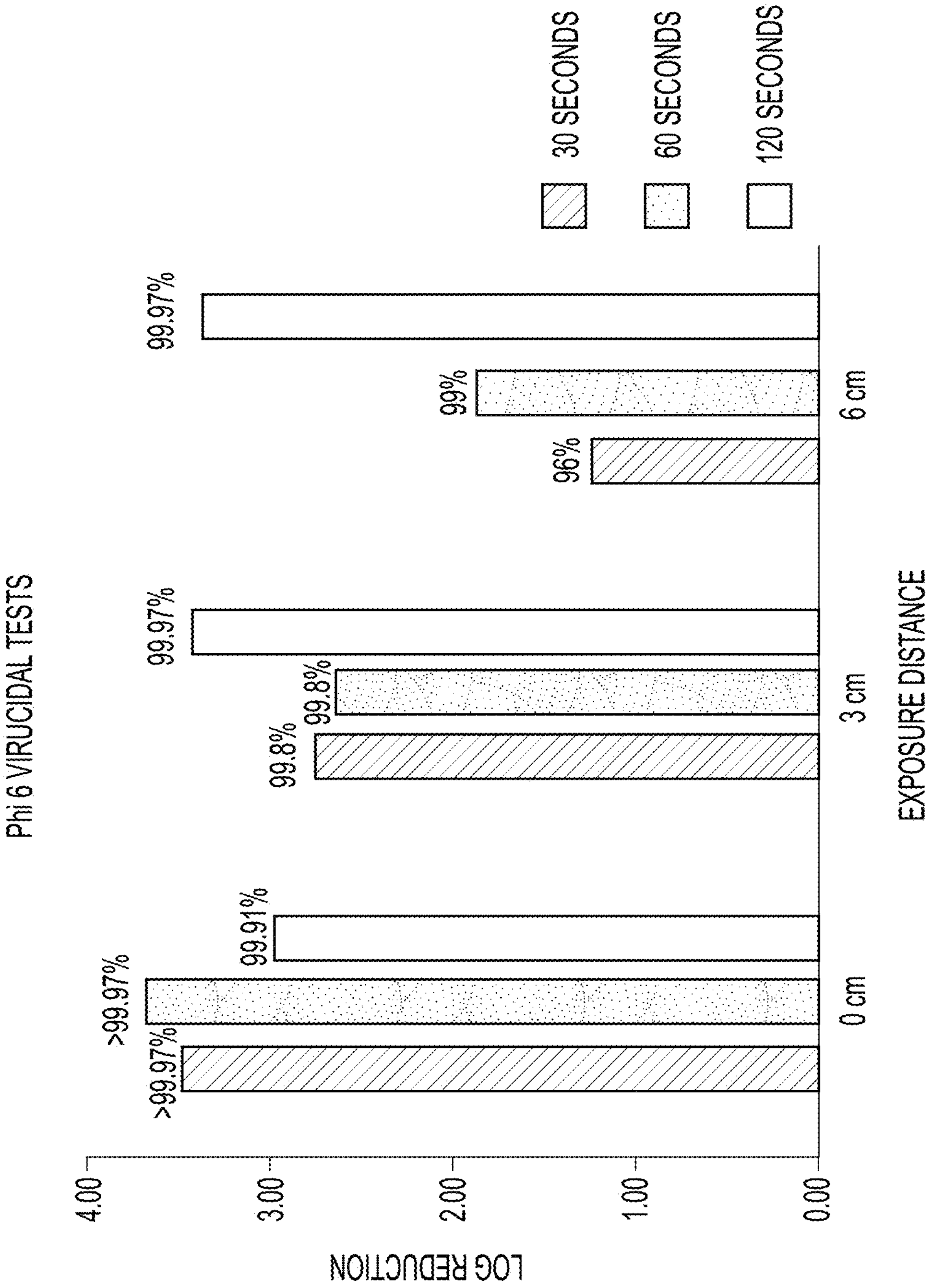
FIG. 8 is a graph showing disinfection results for disinfection of a sample of Phi 6 bacteriophage using the grooming device for animals with asynchronous intermittent light exposure.
Figure 9:
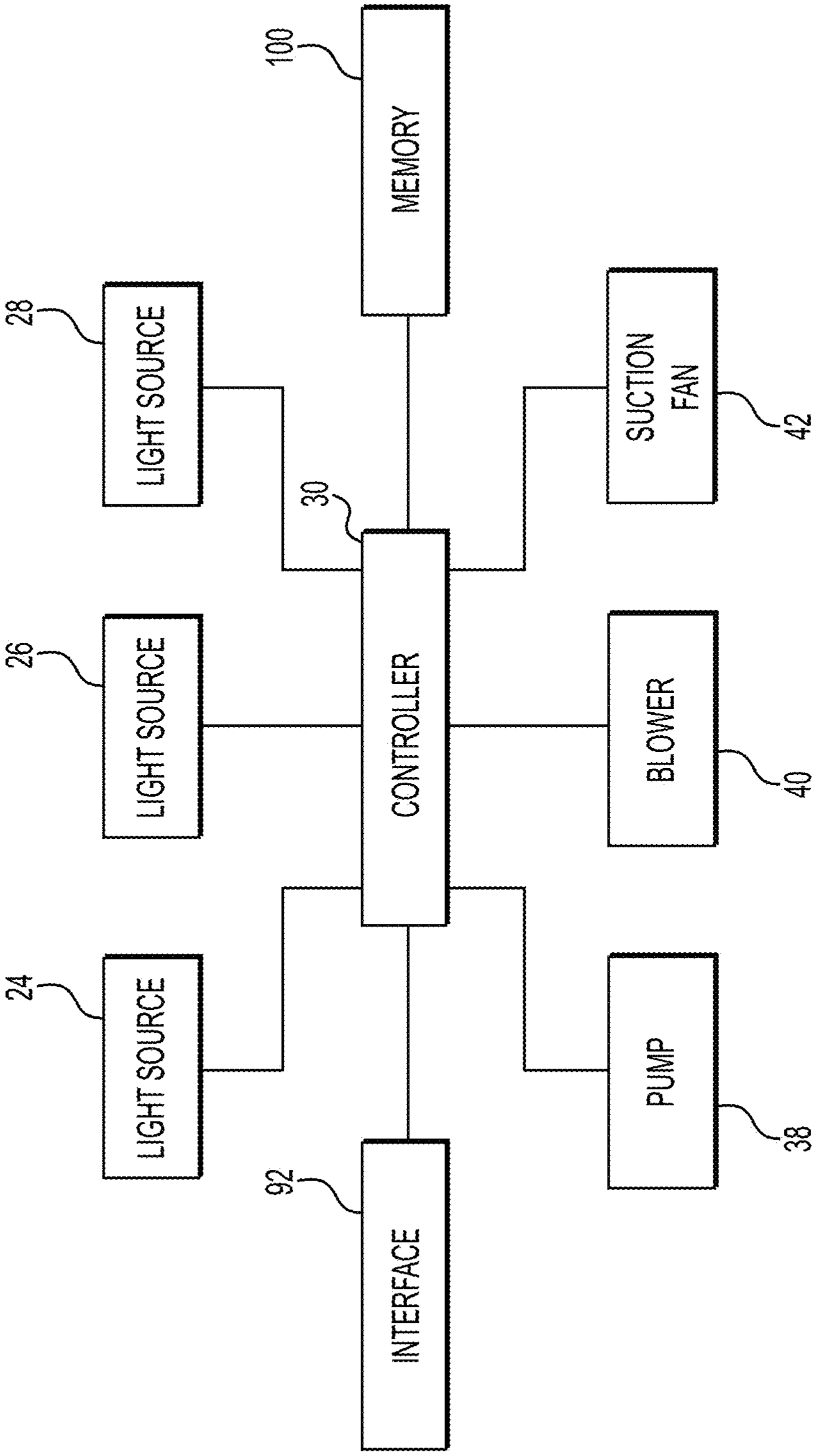
FIG. 9 is a block diagram showing system components of the grooming device for animals with asynchronous intermittent light exposure.

FIG. 8 illustrates the usage of grooming device 10 to disinfect a sample infected with the Phi 6 bacteriophage. Three light sources 24, 26, 28 were used in the test, operating in the following respective wavelength ranges: 285±20 nm (ultraviolet), 405±20 nm (ultraviolet), and 450±20 nm (blue). Controller 30 was programmed to operate light sources 24, 26, 28 as follows: for each cycle of 60 seconds, the 405±20 nm and 285±20 nm light sources were active for the first 48 seconds. These light sources were then deactivated and the 450±20 nm was activated for the last 12 seconds. The cycle was then repeated. As shown in FIG. 8, the greatest disinfection rates occurred at a treatment distance of 0 cm between the device and the sample with a treatment time of 60 seconds, and at distances of 3 cm and 6 cm, each with a treatment time of 120 seconds.

Additional testing of grooming device 10 was performed to test disinfection of samples of the MS2 bacteriophage, *E. coli* bacteria and *S. aureus* bacteria. The wavelength ranges and cycle discussed above with reference FIG. 8 was used for these disinfection tests and the log reductions and disinfection percentages for each are presented below in Table 1.

TABLE 1

Virucidal and Bactericidal Performance

| Distance (cm) | Exposure time (s) | MS2 Log red. | MS2 % | *E. coli* Log red. | *E. coli* % | *S. aureus* Log red. | *S. aureus* % |
|---|---|---|---|---|---|---|---|
| 0 | 30 s | 1.29 | 94.9 | 3.19 | >99.9 | 3.08 | >99.9 |
| | 60 s | 1.84 | 98.6 | 3.29 | >99.9 | 3.15 | >99.9 |
| | 120 s | 2.08 | 99.2 | 3.25 | >99.9 | 3.25 | >99.9 |
| 3 | 30 s | 0.50 | 68.4 | 3.19 | >99.9 | 2.40 | 99.6 |
| | 60 s | 1.06 | 91.3 | 3.13 | >99.9 | 2.99 | 99.9 |
| | 120 s | 1.33 | 95.3 | 3.25 | >99.9 | 3.25 | >99.9 |
| 6 | 30 s | 0.26 | 45.0 | 0.93 | 88.3 | 0.24 | 42.4 |
| | 60 s | 0.75 | 82.2 | 2.61 | 99.8 | 1.87 | 98.6 |
| | 120 s | 0.68 | 79.1 | 2.61 | 99.8 | 2.81 | 99.8 |

Although the above combination used for testing included two ultraviolet wavelength ranges and a blue wavelength range, it should be understood that any suitable combination of wavelength ranges may be used. As a non-limiting example, a combination of ultraviolet, blue and green lights, under the programmable control of controller 30, can provide microbial disinfection, promote healthy skin and enhance wound healing. As another non-limiting example, a combination of ultraviolet, blue and red/infrared lights, under the programmable control of controller 30, can provide microbial disinfection, improve blood circulation and promote a healthy fur and coat. As a further non-limiting example, a combination of ultraviolet and deep blue lights, under the programmable control of controller 30, can provide microbial disinfection and pest repellence. As another non-limiting example, a combination of ultraviolet, deep blue and green lights, under the programmable control of controller 30, can provide microbial disinfection, pest repellence, promote healthy skin, and enhance wound healing. As a further non-limiting example, a combination of ultraviolet, deep blue and red/infrared lights, under the programmable control of controller 30, can provide microbial disinfection, pest repellence, improve blood circulation and promote healthy fur and coat. As another non-limiting example, a combination of ultraviolet, deep blue, green and red/infrared lights, under the programmable control of controller 30, can provide microbial disinfection, pest repellence, enhance healthy skin, improve blood circulation and promote a healthy fur and coat.

As a non-limiting example, a variety of different grooming devices 10 may be manufactured, each including a different combination of light sources. As a further non-limiting example, the grooming device 10 may include all of the above different light sources, with controller 30 being programmed to make use the particular combinations of lights for desired results.

It is to be understood that the grooming device for animals with asynchronous intermittent light exposure is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A grooming device for animals with asynchronous intermittent light exposure, comprising:

a head portion comprising:

a hollow housing having an upper wall, a lower wall and at least one sidewall, the upper wall having a light exposure aperture formed therethrough; and a plurality of light sources received within the hollow housing, wherein each of the light sources produces light with a unique wavelength range, the plurality of light sources being positioned within the hollow housing such that the light generated thereby passes through the light exposure aperture;

a handle portion attached to the head portion;

a grooming accessory releasably attached to the head portion, wherein the grooming accessory comprises a brush, the brush comprising:

a bristle plate releasably attached to the hollow housing; and a plurality of bristles fixed to, and projecting from, the bristle plate, wherein the bristle plate has a light exposure opening formed therethrough, the light exposure opening being aligned with the light exposure aperture when the bristle plate is releasably attached to the hollow housing;

a controller configured to actuate selected ones of the plurality of light sources at preselected times with respect to one another and for preselected intervals;

a pusher plate received within the hollow housing, the pusher plate having opposed upper and lower surfaces;

a push button secured to the lower surface of the pusher plate, wherein the lower wall of the hollow housing has a button opening formed therethrough such that the push button projects outwardly through the button opening;

a pair of rods each having opposed upper and lower ends, the lower ends thereof being secured to the upper surface of the pusher plate, the upper ends thereof being respectively slidably received through a pair of passages formed through the bristle plate; and a fur removal plate having a plurality of slots formed therethrough, the plurality of bristles being slidably received through the slots, and the fur removal plate being releasably attached to the upper ends of the pair of rods, whereby pushing the pusher plate via the push button pushes the fur removal plate with respect to the bristle plate.

2. The grooming device for animals with asynchronous intermittent light exposure as recited in claim 1, wherein the handle portion is releasably attached to the head portion.

3. The grooming device for animals with asynchronous intermittent light exposure as recited in claim 2, wherein the head portion comprises a hollow connection portion for releasable attachment to the handle portion.

4. The grooming device for animals with asynchronous intermittent light exposure as recited in claim 3, wherein the upper wall of the hollow housing has a fluid port formed therein, the hollow connection portion being in fluid communication with the fluid port.

5. The grooming device for animals with asynchronous intermittent light exposure as recited in claim 4, further comprising a pump in communication with the controller, the pump being adapted for selectively and controllably pumping a fluid through the hollow connection portion and the fluid port.

6. The grooming device for animals with asynchronous intermittent light exposure as recited in claim 4, further comprising a blower in communication with the controller, the blower being adapted for selectively and controllably blowing air through the hollow connection portion and the fluid port.

7. The grooming device for animals with asynchronous intermittent light exposure as recited in claim 4, further comprising a suction fan in communication with the controller, the suction fan being adapted for selectively and controllably sucking air through the fluid port and the hollow connection portion.

8. The grooming device for animals with asynchronous intermittent light exposure as recited in claim 1, further comprising a pair of springs wrapped around the pair of rods between the pusher plate and the upper wall of the hollow housing.

* * * * *